US00PP30492P3

(12) United States Plant Patent
Hancock

(10) Patent No.: US PP30,492 P3
(45) Date of Patent: May 14, 2019

(54) STRAWBERRY PLANT NAMED 'WASATCH'

(50) Latin Name: *Fragaria x ananassa*
Varietal Denomination: Wasatch

(71) Applicant: Board of Trustees of Michigan State University, East Lansing, MI (US)

(72) Inventor: James Hancock, Scarborough, ME (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/530,810

(22) Filed: Mar. 3, 2017

(65) Prior Publication Data

US 2018/0255672 P1 Sep. 6, 2018

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
See application file for complete search history.

(56) References Cited

PUBLICATIONS

"MSU Releases New Strawberries: Redstart & Wasatch", posted on Dec. 27, 2016; http://www.technologies.msu.edu/msu-releases-new-strawberries-redstart-wasatch, accessed on Jul. 18, 2017.
"Wasatch Day-Neutral Strawberry—MSU 68", http://msut.technologypublisher.com/technology/22785 accessed on Jul. 18, 2017.

*Primary Examiner* — Keith O. Robinson
(74) *Attorney, Agent, or Firm* — McKee, Voorhees & Sease, PLC

(57) ABSTRACT

A new and distinct *Fragaria* x *ananassa* plant named 'Wasatch', particularly characterized as a strong day-neutral.

2 Drawing Sheets

Botanical name of the genus and species of the plant claimed: The strawberry of this invention is botanically identified as *Fragaria* x *ananassa*.

Variety denomination: The variety denomination is 'Wasatch'.

BACKGROUND OF THE INVENTION

The present invention relates to a new and distinct variety of a strawberry plant, botanically known as *Fragaria* x *ananassa* of the Rosaceae family, and hereinafter referred to by the variety denomination 'Wasatch'.

The new *Fragaria* x *ananassa* variety is a product of a planned breeding program conducted by the inventors. The objective of the breeding program was to develop a new *Fragaria* x *ananassa* variety intended for the Midwestern and Northeastern USA, Ontario and Quebec, and the Pacific Northwest.

The new variety originated from a cross between female parent 'Seascape' (U.S. Plant Pat. No. 7,614) and male parent MSU 38 (unpatented)(itself the product of a cross between 'Tribute' (unpatented) and 'Honeoye' (unpatented)) made in a greenhouse at Michigan State University, East Lansing, Mich. in March 2008. 'Wasatch' was first selected in the summer of 2009 from a family of 93 planted in an open field in Benton Harbor, Mich. It was re-evaluated in the same field the following season, and was originally designated as MSU 68.

Asexual propagation of the new *Fragaria* x *ananassa* variety by runners was performed at Michigan State University, East Lansing, Mich. in the fall of 2010 where runners from the original mother plant were dug and transferred to a greenhouse. The potted plants were allowed to runner in the summer of 2011 and 2013, and the resulting daughter plants were rooted in sterilized soil. These plants were encouraged to go dormant each winter by leaving the greenhouse unheated.

Horticultural examination has demonstrated that the combination of characteristics as herein disclosed for the new variety was firmly fixed and retained through successive generations of asexual propagation. The new variety propagates true-to-type.

BRIEF DESCRIPTION OF THE INVENTION

The following traits have been repeatedly observed and are determined to be characteristics of 'Wasatch', which in combination, distinguish this strawberry plant as a new, unique and distinct variety: Strong day-neutral, firm, high yields, superior fruit color, greater plant vigor, and excellent flavor.

In comparison to the parental varieties, 'Seascape' (U.S. Plant Pat. No. 7,614) and MSU 38, 'Wasatch' differs primarily in the traits listed in Table 1.

TABLE 1

Comparison with parent varieties

| Trait | Female Parent 'Seascape' | Male Parent MSU 38 | 'Wasatch' |
|---|---|---|---|
| Fruiting period | Day-neutral | Short-day | Day-neutral |
| Vigor | Low | High | High |
| Fruit shape | Long wedge | Globose conic | Conic |

In field trials over three seasons, 'Wasatch' has performed as a strong day-neutral, fruiting an average of 12 weeks in Mt. Vernon, Wash. and 8 weeks at Benton Harbor, Mich. 'Wasatch' compares favorably to the most widely planted day-neutrals 'Seascape' and 'Albion' (U.S. Plant Pat. No. 16,228) developed in California. 'Wasatch' has a slightly paler internal color than 'Seascape' and similar firmness; however, it is superior in yield, vigor, fruit size and flavor. 'Wasatch' is not as firm and is smaller fruited than 'Albion', but it has higher yields, better fruit color, greater plant vigor and similar excellent flavor. 'Wasatch' did not display any symptoms of common diseases in the field trials. Description of field trials is below.

Trials

Ten plants of 'Wasatch' were planted in 2012 and 2014 with other MSU selections in an open field in Benton Harbor, Mich. and in Burlington, Wash. under high tunnels. Plants were maintained on a black plastic mulch in raised beds in Burlington, Wash., while in Benton Harbor, Mich. they were grown on flat beds without mulch. All flowers were removed from the first flush of blooms in the planting year. Adjacent to these trials were other plantings of the day-neutral cultivars 'Albion' and 'Seascape'. The plants set in 2012 were evaluated in years one and two for weeks of fruiting, vigor, fruit size, productivity and fruit quality. The plants set in 2014 were evaluated for the same parameters in just that year.

Ten plants of 'Wasatch' were also planted with other MSU selections under a high tunnel in Benton Harbor, Mich. in April of 2012. Adjacent to this planting was a replicated trial of 8 day-neutral cultivars including 'Albion' and 'Seascape'. The plants were set in raised beds on white plastic mulch on top of black plastic mulch. Flowers were removed from each plant until early July and fruit were harvested weekly for the rest of the season. The same planting was evaluated the following year for vigor, productivity and fruit quality.

Results

Michigan Open Field Trials (2012-2013):

In the open field trials in Michigan in 2012 and 2013, 'Wasatch' was acceptable to superior for all the rated characteristics and fruited for 8 weeks in both years (Table 2).

In 2012, 'Wasatch' had higher yields and better flavor than 'Seascape', and was comparable for all the other characteristics except internal color. 'Wasatch' fruit were smaller and slightly less firm than 'Albion', but it had comparable yields, higher vigor and better color.

In the second harvest season, 'Wasatch' was much more vigorous than 'Seascape' and had larger fruit with better appearance and flavor. It had comparable firmness, but slightly lower yields and paler color. 'Wasatch' was more vigorous, had better fruit color and was much higher yielding than 'Albion', although it was smaller fruited and less firm.

Overall, the fruit size, vigor and yield of the three cultivars were reduced in 2013 compared to 2012; however, 'Wasatch' was less affected than 'Albion' and 'Seascape' for vigor and yield and 'Seascape' for fruit size. The year 2013 was unusually hot in Michigan, suggesting that 'Wasatch' may be more resistant to high temperatures than 'Seascape' and 'Albion', but more data is needed to confirm this.

TABLE 2

Strawberry trials in the open field in Benton Harbor, MI in 2012 and 2013.

| | | Cultivar | | |
|---|---|---|---|---|
| Year | Characteristic | 'Albion' | Wasatch' | 'Seascape' |
| 2012 | Plant vigor | 7[a] | 8 | 8 |
| | Total Yield | 9 | 9 | 7 |
| | Fruit size | 9 | 7 | 7 |
| | Fruit appearance | 8 | 8 | 8.5 |
| | External color | 6 | 8 | 8 |
| | Internal color | 7 | 7 | 8 |
| | Firmness | 9 | 8 | 8 |
| | Flavor | 8 | 7 | 6 |
| 2013 | Plant vigor | 4 | 7 | 6 |
| | Total Yield | 3 | 6 | 7 |
| | Fruit size | 7 | 4 | 3 |
| | Fruit appearance | 8 | 8 | 7 |
| | External color | 7 | 8 | 9 |
| | Internal color | 7 | 7 | 8 |
| | Firmness | 10 | 8 | 8 |
| | Flavor | 7 | 7.5 | 6 |

[a]1 = poor; 7 = commercially acceptable; 10 = superior.

Washington Tunnel Trials (2012-2013):

In the tunnel trials in Washington in 2012 and 2013, all the characteristics of 'Wasatch' were rated acceptable to superior (Table 3). 'Wasatch' fruited for 11 weeks in 2012 and 13 weeks in 2013.

In 2012, 'Wasatch' had higher vigor, larger fruit size, better appearance and much better flavor than 'Seascape'. It was comparable for all the other characteristics measured. 'Wasatch' was better colored than 'Albion' and had higher yields, more attractive fruit and higher vigor. Its fruit were smaller and less firm, but it had comparable flavor.

In the second harvest season, 'Wasatch' was more vigorous than 'Seascape' and had comparable firmness, yield and flavor. Its internal color was somewhat paler. 'Wasatch' had superior vigor, yield and internal color compared to 'Albion', with comparable fruit appearance and external color. Its fruit size and firmness were less than 'Albion'.

TABLE 3

Strawberry trials in hoop houses in Mt. Vernon, WA in 2012 and 2013.

| | | Cultivar | | |
|---|---|---|---|---|
| Year | Characteristic | 'Albion' | Wasatch' | 'Seascape' |
| 2012 | Plant vigor | 7[a] | 9 | 7 |
| | Weeks of fruiting | — | 11 | — |
| | Total Yield | 8 | 9 | 9 |
| | Fruit size | 9 | 8 | 7 |
| | Fruit appearance | 8 | 9 | 8 |
| | External color | 8 | 9 | 9 |
| | Internal color | 6 | 8 | 8 |
| | Firmness | 10 | 9 | 9 |
| | Flavor | 8 | 8 | 6 |
| 2013 | Plant vigor | 8 | 9 | 8 |
| | Weeks of fruiting | — | 13 | — |
| | Total Yield | 8 | 9 | 9 |
| | Fruit size | 10 | 7 | 7 |
| | Fruit appearance | 8 | 8 | 8 |
| | External color | 8 | 8 | 8.5 |
| | Internal color | 6 | 7 | 8 |
| | Firmness | 10 | 8 | 8 |
| | Flavor | 9 | 8 | 8 |

[a]1 = poor, 7 = commercially acceptable, 10 = superior

Michigan Tunnel Trials (2012-2013):

In the tunnels in Benton Harbor, Mich. in 2012, 'Wasatch' had acceptable to superior ratings for all characteristics, except external color, which was just below the accepted standard (6.5 vs. 7.0)(Table 4). It produced fruit for 13 weeks. 'Wasatch' had greater plant vigor, much higher yields, larger berries, more attractive fruit and was better flavored than 'Seascape' (Table 4). Its fruit were not as deeply colored, but it was comparable in firmness. 'Wasatch' also had greater plant vigor and higher yields than 'Albion', although its fruit were less firm. 'Wasatch' was in general lower yielding than 'Albion' and 'Seascape' in the first half of the season, but much higher yielding in the second half.

In 2013, 'Wasatch' had acceptable ratings for all characteristics except fruit size and yield (Table 4). However, it had larger fruit than 'Seascape' and comparable yields (Table 4). The fruit of 'Wasatch' were smaller than 'Albion', but its yields were much higher. 'Wasatch' was more flavorful than 'Seascape' with comparable firmness. Its fruit were less firm than 'Albion', but better colored and slightly better flavored.

TABLE 4

Strawberry trials in hoop houses in Benton Harbor, MI in 2012 and 2013.

| | | Cultivar | | |
|---|---|---|---|---|
| Year | Characteristic | 'Albion' | 'Wasatch' | 'Seascape' |
| 2012 | Plant vigor | 5[1] | 7 | 6 |
| | g/plant | 504 | 604 | 481 |
| | g/berry | 10.7 | 9.5 | 6.4 |
| | Fruit appearance | 7 | 8 | 6 |
| | External color | 7 | 6.5 | 8 |
| | Internal color | 7 | 8 | 8 |
| | Firmness | 10 | 8 | 8 |
| | Flavor | 7.5 | 7 | 6 |
| 2013 | Plant vigor | 4 | 7 | 6 |
| | Total Yield | 3 | 6 | 6 |
| | Fruit size | 7.5 | 4 | 3 |
| | Fruit appearance | 8 | 9 | 7 |
| | External color | 7 | 7 | 9 |
| | Internal color | 7 | 8 | 8 |
| | Firmness | 9 | 8 | 8 |
| | Flavor | 7 | 7.5 | 6 |

[a]1 = poor, 7 = acceptable commercial quality, 10 = excellent

Michigan Open Field Trials (2014):

In 2014 in Michigan, Wasatch had acceptable to superior ratings for all characteristics (Table 5). The fruit of 'Wasatch' were smaller than 'Albion' and less firm, but it had higher vigor, yields, better appearance and color; it was comparable for flavor. In Washington, 'Wasatch' fruit were less firm than 'Albion', but their size was comparable and Wasatch had better appearance and internal color.

TABLE 5

Strawberry trials in under hoops in Mt. Vernon, WA and in open fields in Benton Harbor, MI in 2014.

| | | Cultivar | |
|---|---|---|---|
| Location | Characteristic | 'Albion' | 'Wasatch' |
| MI | Plant vigor | 7[a] | 9 |
| | Total Yield | 7 | 7 |
| | Fruit size | 8 | 7 |
| | Fruit appearance | 8 | 9 |

TABLE 5-continued

Strawberry trials in under hoops in Mt. Vernon, WA and in open fields in Benton Harbor, MI in 2014.

| | | Cultivar | |
|---|---|---|---|
| Location | Characteristic | 'Albion' | 'Wasatch' |
| | External color | 6 | 8 |
| | Internal color | 7 | 7 |
| | Firmness | 9 | 8 |
| | Flavor | 8 | 8 |
| WA | Plant vigor | 8 | 9 |
| | Total Yield | 7 | 9 |
| | Fruit size | 8 | 8 |
| | Fruit appearance | 7 | 9 |
| | External color | 9 | 9 |
| | Internal color | 7 | 8 |
| | Firmness | 9 | 8 |
| | Flavor | 8 | 7 |

[a]1 = poor, 7 = acceptable commercial quality, 10 = excellent

Except for fruit size in the second season of the hoop trials in Michigan, all the horticultural characteristics of 'Wasatch' proved acceptable to superior. It was generally superior to 'Seascape' in vigor, yield, fruit size, fruit appearance and flavor. It had comparable firmness and was slightly less colored than 'Seascape'. 'Wasatch' was superior to 'Albion' in vigor, yield, fruit appearance, and fruit color. It was smaller fruited and less firm than 'Albion', but had similar excellent flavor.

BRIEF DESCRIPTION OF THE PHOTOGRAPHS

The accompanying photographs illustrate the overall appearance of the new *Fragaria* x *ananassa* variety 'Wasatch' showing the colors as true as is reasonably possible with colored reproductions of this type. Colors in the photographs may differ slightly from the color values cited in the detailed morphological description, which accurately describe the color of 'Wasatch'. Plants were set in the field in April and the photographs taken in June.

DETAILED BOTANICAL DESCRIPTION

Figure 1:
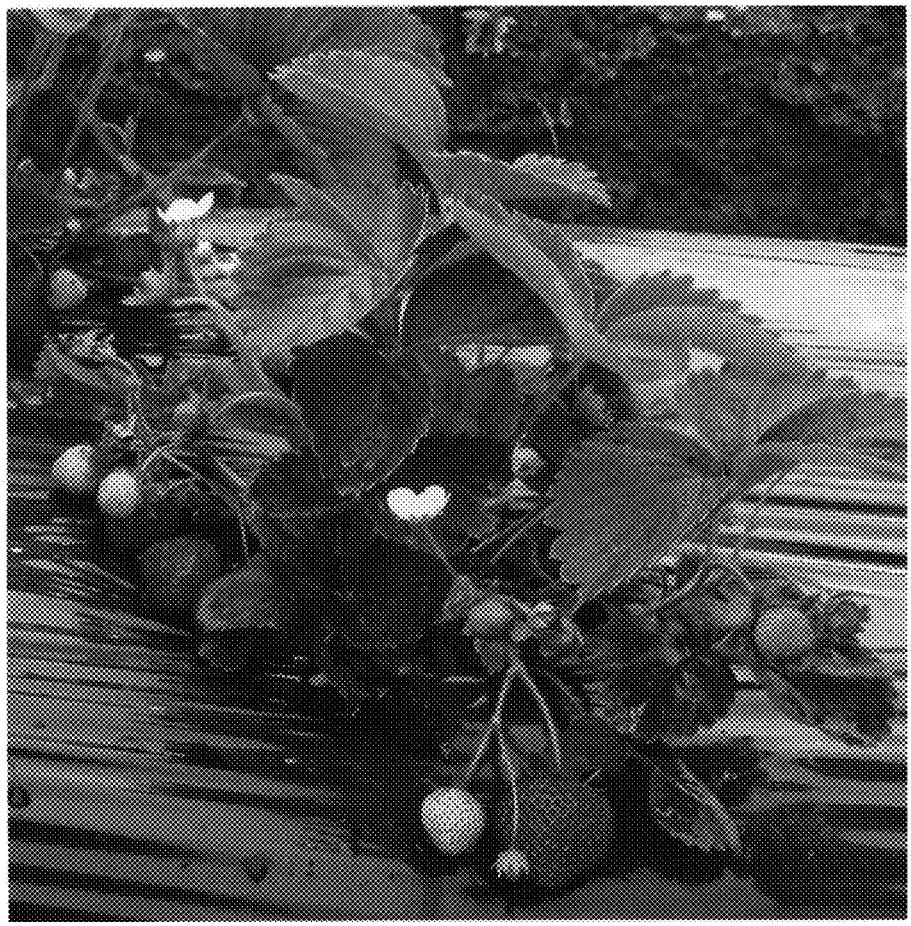
FIG. 1 shows a typical fruit bearing plant of 'Wasatch' with flowers.
Figure 2:
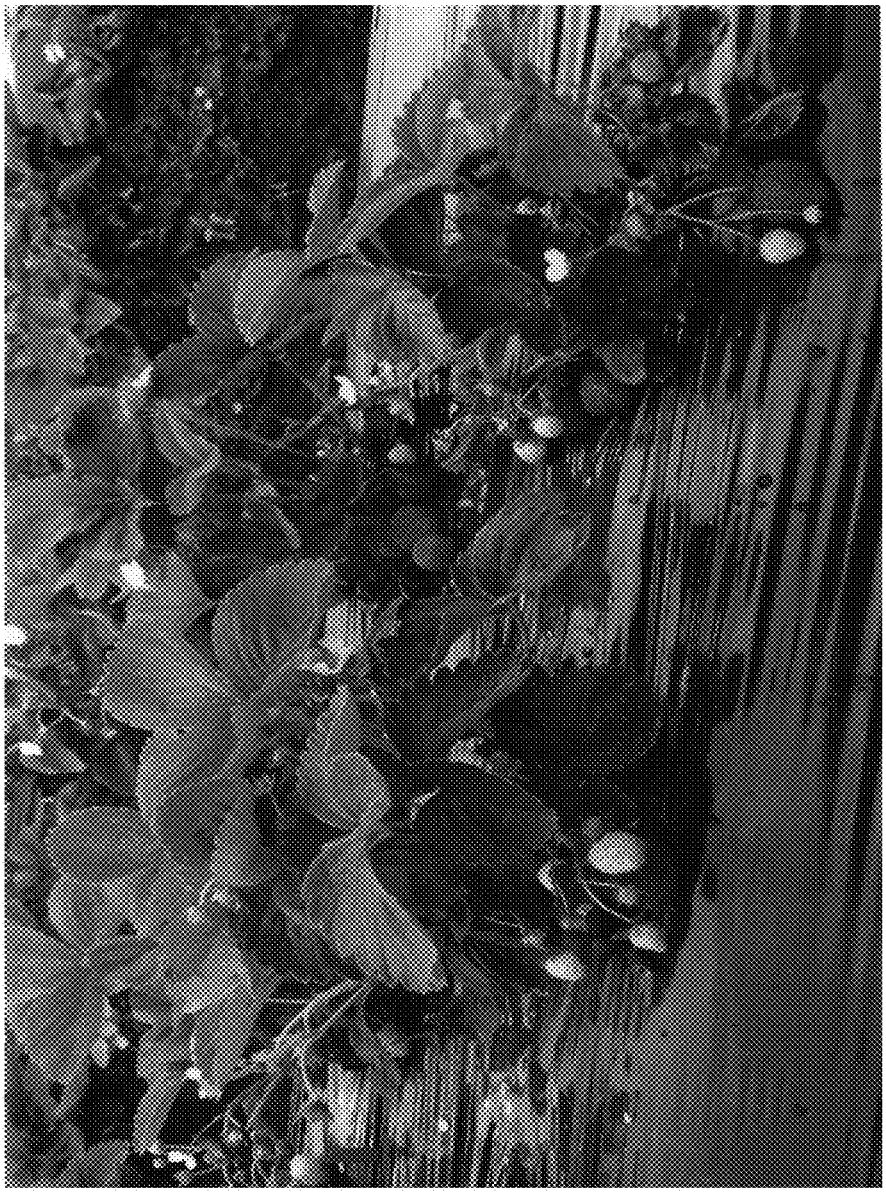
FIG. 2 shows a typical row of 'Wasatch' planted in the field.

The new *Fragaria* x *ananassa* 'Wasatch' has not been observed under all possible environmental conditions. The phenotype of the new variety may vary with variations in environment such as temperature, light intensity, day length or soil without any change in the genotype of the strawberry plant.

The aforementioned photographs, together with the following observations, measurements and values describe plants of 'Wasatch' as grown in the field in Benton Harbor, Mich., under conditions which closely approximate those generally used in commercial practice. The described plants were propagated from stolons and planted at a distance of 25 cm in sandy red loam soil at an elevation of about 30 meters above sea level, with drip irrigation and fertilizers as generally used in commercial practice. Average annual precipitation is about 550 mm, with an average 350 mm of precipitation in winter (December to February). Mean diurnal minimum temperature in January is −8° C., and mean diurnal maximum temperature in July is 24° C.

Mother plants were planted in the beginning of May, in the field nursery at 2.5 m×2.5 m distance. Overhead irrigation with addition of fertilizers was used. The average day/night temperatures during the establishment of the daughter plants, between June to August, are 32° C./18° C. respectively. Runners appeared from June, which produce young daughter plants up till mid-September Unless otherwise stated, the detailed morphological description includes observations, measurements and values taken from May to June, 2014 and based on 'Wasatch' plants grown in a greenhouse at Michigan State University. Quantified measurements are expressed as an average or a range of measurements taken from a number of plants of 'Wasatch'. The measurements of any individual plant or any group of plants, of the new variety may vary from the stated average or range.

Color references are made to The Royal Horticultural Society Colour Chart (R.H.S.), (1986 edition), except where general colors of ordinary significance are used. All of the plants of 'Wasatch', insofar as they have been observed, have been consistent in all the characteristics described below.

TABLE OF CHARACTERISTICS

Classification:
- *Botanical.*—*Fragaria* x *ananassa.*

Parentage:
- *Female or seed parent.*—'Seascape' (U.S. Plant Pat. No. 7,614).
- *Male or pollen parent.*—MSU 38 (Unpatented).

Propagation: By runners in a greenhouse at Michigan State University.

Foliar characteristics in mid-summer:
- *Plant height* (*mm*).—15.6 (16-21).
- *Plant spread* (*mm*).—32.8 (30-34).
- *Growth habit.*—Upright.
- *Color.*—137D.
- *Leaf division.*—Three leaflets.
- *Mid-tier leaflet length* (*mm*).—73.4 (70-85).
- *Shape* (*length/width*).—58.6 (46-65).
- *Basal angle of terminal leaflet.*—23.6 (19-30).
- *Serrations of terminal leaflet.*—21.0 (19-25).
- *Serrations per leaf.*—64.8 (62-72).
- *Petiolule length* (*mm*).—8.2 (6-10).
- *Petiole length* (*mm*).—149.4 (132-160).
- *Petiole diameter* (*mm*).—3.0 (2.5-3.5).
- *Petiole color.*—145B.
- *Venation.*—Pinnate.
- *Leaf pubescence.*—None to sparse on lower surface.
- *Leaf blistering.*—Absent.
- *Leaf glossiness.*—Medium.
- *Petiole pubescence.*—Moderate.
- *Petiole pubescence direction.*—Perpendicular.
- *Position of the inflorescence in relation to the foliage.*—Same level.
- *Number of stolons.*—1-4.

Flowering and fruiting characteristics:
- *Flowers per truss.*—6.0 (5-8).
- *Flower position.*—Most exposed.
- *Petal width* (*mm*).—7.2 (6.8-8.4).
- *Petal color.*—White.
- *Petal shape.*—Actinomorphic.
- *Petal arrangement.*—Free.
- *Calyx diameter* (*mm*).—27.5 (25-31).
- *Corolla diameter* (*mm*).—20.7 (23.5-26.7).
- *Size of the calyx in relation to the corolla.*—Smaller.
- *Sepal length* (*mm*).—11.8 (10.5-14.5).
- *Sepal width* (*mm*).—4.6 (3.5-5.0).
- *Sepal color.*—146A.
- *Stamens.*—Present.
- *Number of stamens.*—10-15.
- *Pedicle length* (*mm*).—31.4 (27-54).
- *Pedicle diameter* (*mm*).—1.7 (1.0-2.0).
- *Pedicle color.*—146D.
- *Fruit width* (*mm*).—35.8 (32-40).
- *Fruit length* (*mm*).—32.3 (28-35).
- *Length/width.*—0.9 (0.7-1.0).
- *Fruit shape.*—Conic.
- *Firmness of the fruit.*—Firm.
- *Size* (*g/frt*).—13.8 (9.8-15.20).
- *Calyx diameter* (*mm*).—16.5 (12.7-19.2).
- *Calyx position.*—Even with base of fruit.
- *External color.*—45A.
- *Internal color.*—34A.
- *Depth of color.*—50%.
- *Fruit per truss.*—6.0 (5-8).
- *Achene color.*—163B (pale tan).
- *Achene placement.*—Level.
- *Time of beginning of flowering.*—Mid-April.

Fruit quality measurements:
- *Soluble solids* (%).—10.2.
- *Titratable acidity* (%).—1.04 (0.99-1.08).

What is claimed is:

1. A new and distinct variety of *Fragaria* x *ananassa* plant named 'Wasatch', as illustrated and described herein.

* * * * *